(12) United States Patent
McIff et al.

(10) Patent No.: US 12,029,460 B2
(45) Date of Patent: *Jul. 9, 2024

(54) COMPACT ORTHOPEDIC ANTI-ROTATION DEVICE

(71) Applicant: University of Kansas, Lawrence, KS (US)

(72) Inventors: Terence Edward McIff, Olathe, KS (US); Edward Bruce Toby, Overland Park, KS (US)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/484,736

(22) Filed: Sep. 24, 2021

(65) Prior Publication Data

US 2022/0008108 A1 Jan. 13, 2022

Related U.S. Application Data

(60) Continuation of application No. 15/819,073, filed on Nov. 21, 2017, now Pat. No. 11,129,656, which is a
(Continued)

(51) Int. Cl.
*A61B 17/86* (2006.01)
*A61B 17/064* (2006.01)
(Continued)

(52) U.S. Cl.
CPC ...... *A61B 17/8685* (2013.01); *A61B 17/0642* (2013.01); *A61B 17/68* (2013.01);
(Continued)

(58) Field of Classification Search
CPC . A61B 17/8685; A61B 17/0642; A61B 17/68; A61B 17/064; A61B 17/0644;
(Continued)

(56) References Cited

U.S. PATENT DOCUMENTS 4,014,492 A 3/1977 Rothfuss
4,261,244 A 4/1981 Becht et al.
(Continued)

FOREIGN PATENT DOCUMENTS

CN 101983136 3/2011
EP 0812167 5/2003
(Continued)

OTHER PUBLICATIONS

U.S. Appl. No. 61/586,075, filed Jan. 12, 2012, McIff.
(Continued)

*Primary Examiner* — Marcela I. Shirsat
(74) *Attorney, Agent, or Firm* — RAY QUINNEY & NEBEKER P.C.; Paul N. Taylor

(57) ABSTRACT

Embodiments of the present invention relate to systems, methods, and apparatus for immobilizing and/or securing bone portions. Particularly, at least one embodiment involves a compact anti-rotation device that can secure adjacent bones and/or bone portions in a manner that prevents or limits relative rotational movement thereof.

22 Claims, 5 Drawing Sheets

Related U.S. Application Data division of application No. 13/741,263, filed on Jan. 14, 2013, now Pat. No. 11,033,311.

(60) Provisional application No. 61/586,075, filed on Jan. 12, 2012.

(51) Int. Cl.
*A61B 17/68* (2006.01)
*A61B 17/00* (2006.01)
*A61B 17/17* (2006.01)

(52) U.S. Cl.
CPC .. *A61B 17/869* (2013.01); *A61B 2017/00004* (2013.01); *A61B 17/064* (2013.01); *A61B 2017/0641* (2013.01); *A61B 2017/0645* (2013.01); *A61B 17/1782* (2016.11)

(58) Field of Classification Search
CPC ... A61B 17/072; A61B 17/08; A61B 17/1782; A61B 17/0401; A61B 2017/0647; A61B 2017/0641; A61B 2017/0645
USPC .......................................... 606/300, 301, 75
See application file for complete search history.

(56) References Cited

U.S. PATENT DOCUMENTS

| | | | |
|---|---|---|---|
| 4,275,813 A | 6/1981 | Noiles | |
| 4,425,780 A | 1/1984 | Champoux | |
| 4,428,376 A | 1/1984 | Mericle | |
| 4,485,816 A * | 12/1984 | Krumme | A61B 17/0644 411/909 |
| 4,489,875 A | 12/1984 | Crawford et al. | |
| 4,505,273 A | 3/1985 | Braun et al. | |
| 4,569,128 A | 2/1986 | Thomas | |
| 4,570,623 A * | 2/1986 | Ellison | A61B 17/68 606/75 |
| 4,610,251 A | 9/1986 | Kumar | |
| 4,655,222 A | 4/1987 | Florez et al. | |
| 4,714,187 A | 12/1987 | Green | |
| 4,722,161 A | 2/1988 | Young | |
| 5,158,567 A | 10/1992 | Green | |
| 5,324,307 A | 6/1994 | Jarrett et al. | |
| 5,364,406 A | 11/1994 | Sewell, Jr. | |
| 5,366,479 A | 11/1994 | McGarry et al. | |
| 5,423,857 A | 6/1995 | Rosenman et al. | |
| 5,527,319 A | 6/1996 | Green et al. | |
| 5,636,398 A | 6/1997 | Fike | |
| 5,720,755 A | 2/1998 | Dakov | |
| 5,725,554 A | 3/1998 | Simon et al. | |
| 5,738,474 A | 4/1998 | Blewett | |
| 6,273,903 B1 | 8/2001 | Wilk | |
| 7,108,709 B2 | 9/2006 | Cummins | |
| 7,429,265 B2 | 9/2008 | O'Malley et al. | |
| 7,673,781 B2 | 3/2010 | Swayze et al. | |
| 7,891,531 B1 | 2/2011 | Ward | |
| 8,210,415 B2 | 7/2012 | Ward | |
| D780,311 S | 2/2017 | Cheney et al. | |
| 10,117,647 B2 | 11/2018 | Cheney | |
| 11,129,656 B2 * | 9/2021 | McIff | A61B 17/8685 |
| 2003/0167596 A1 | 9/2003 | Gabriel | |
| 2005/0216036 A1 | 9/2005 | Nakao | |
| 2005/0234510 A1 | 10/2005 | Zamierowski | |
| 2007/0194079 A1 | 8/2007 | Hueil et al. | |
| 2007/0239278 A1 | 10/2007 | Heinz | |
| 2008/0082125 A1 | 4/2008 | Murray et al. | |
| 2008/0232929 A1 | 9/2008 | Jackson et al. | |
| 2008/0306480 A1 * | 12/2008 | Wilson | A61B 17/1782 606/280 |
| 2008/0319443 A1 * | 12/2008 | Focht | A61B 17/0642 606/75 |
| 2009/0005807 A1 | 1/2009 | Hess et al. | |
| 2009/0005808 A1 | 1/2009 | Hess et al. | |
| 2009/0182374 A1 | 7/2009 | Keith | |
| 2009/0216233 A1 * | 8/2009 | Wiedrich | A61L 31/044 606/151 |
| 2009/0287145 A1 | 11/2009 | Cragg et al. | |
| 2010/0256675 A1 | 10/2010 | Romans | |
| 2010/0264192 A1 * | 10/2010 | Marczyk | A61B 17/068 227/176.1 |
| 2010/0327042 A1 | 12/2010 | Amid et al. | |
| 2011/0042439 A1 | 2/2011 | Johnson et al. | |
| 2011/0319935 A1 | 12/2011 | Moskowitz et al. | |
| 2012/0203340 A1 * | 8/2012 | Choinski | A61B 17/0401 623/13.14 |
| 2020/0038076 A1 | 2/2020 | Amis et al. | |
| 2020/0197005 A1 | 6/2020 | Daniel | |

FOREIGN PATENT DOCUMENTS

| | | |
|---|---|---|
| EP | 0703757 | 8/2003 |
| EP | 1342439 | 9/2003 |
| EP | 1964528 | 9/2008 |
| GB | 190711589 | 4/1908 |
| GB | 211266 | 2/1924 |
| JP | 2010525949 | 7/2010 |
| KR | 20090027188 | 3/2009 |
| WO | WO0030556 | 6/2000 |
| WO | WO2007117908 | 10/2007 |
| WO | WO2008140439 | 11/2008 |
| WO | WO2009114779 | 9/2009 |

OTHER PUBLICATIONS

Carpenter, et al; "Using a hook plate as alternate fixation for fifth metatarsal base fracture"; The Journal of Foot and Ankle Surgery, vol. 42, Issue 5, 2003, pp. 315-316.

Marcacci, et al; "High Tibial Osteotomy; The Italian Experience"; Operative Techniques in Orthopaedics; vol. 17, Issue 1, 2007, pp. 22-28.

Segal, et al.; "The Stone Table Staple Modification for Obtaining Firm Bone Fixation"; Clinical Orthopaedics and Related Research, p. 340.

Slone, et al.; "Orthopedic Fixation Devices"; Radiographics, Sep. 1991; pp. 823-847.

Stratum Foot Plating System, Zimmer Biomet, retrieved from https://www.zimmerbiomet.com/en/products-and-solutions/specialties/foot-and-ankle/stratum-foot-plating-system.html#10-Info on Dec. 6, 2022, 13 pages.

TriMed Ortho, retrieved from http://trimedortho.com/products, on Dec. 6, 2022, 52 pages.

* cited by examiner

Pair Group 1

Pair Group 2

Pair Group 3

Pair Group 4

Pair Group 5

Pair Group 6

COMPACT ORTHOPEDIC ANTI-ROTATION DEVICE

CROSS-REFERENCE TO RELATED APPLICATIONS

The present application is a continuation of U.S. patent application Ser. No. 15/819,073, filed Nov. 21, 2017, which is a divisional of U.S. patent application Ser. No. 13/741,263, filed Jan. 14, 2013, now U.S. Pat. No. 11,033,311, which claims the benefit of and priority to U.S. Provisional Patent Application No. 61/586,075, filed Jan. 12, 2012, entitled "Inline, Multi-Tine Staple For Orthopedic Surgical Applications," the entire contents of which are incorporated herein by this reference.

BACKGROUND OF THE INVENTION

1. The Field of the Invention

This invention relates to systems, methods, and apparatus for securing bone portions.

2. Background and Relevant Art

Various injuries and/or age-related conditions can affect bones, ligaments, and joint health in a manner that may require medical intervention. For instance, an injury to a ligament can result in separation or dissociation of bones previously connected by a ligament. Among other things, such injuries can lead to loss of mobility as well as discomfort or pain. Therefore, it is commonly desirable to repair damaged ligaments and to realign the bones into normal (e.g., pre-injury) anatomical positions.

For example, tear of scapholunate interosseous ligament ("SLIL"), which connects the scaphoid and lunate bones of the wrist, can affect the patient's wrist movement and mobility. In some instances, the SLIL can be repaired with surgery (e.g., by reconnecting the scaphoid and lunate bones). To heal properly, however, the scaphoid and lunate bones may have to remain substantially immobilized relative to each other.

Commonly used devices and methods for immobilizing the scaphoid and lunate bones are imperfect. Specifically, a patient's ordinary wrist movements normally rotate the scaphoid and lunate bones relative to each other. Hence, typical devices for restricting such rotation experience torque applied thereon by the movement of the patient's wrist. In some instances, such devices cannot fully absorb the applied torque and, thus, permit rotation of the scaphoid and lunate bones. As mentioned above, rotation of the scaphoid and lunate bones can interfere with the healing of the repaired ligament and can result in further injury.

Accordingly, there are a number of disadvantages in current devices and methods used for immobilizing relative movement and/or rotation of bones that can be addressed.

BRIEF SUMMARY

Embodiments of the present invention provide systems, methods, and apparatus for immobilizing and/or securing bone portions. Particularly, at least one embodiment involves a compact anti-rotation device that can secure adjacent bones and/or bone portions in a manner that prevents or limits relative rotational movement thereof. Accordingly, the compact anti-rotation device can help promote healing of reconnected bone portions, which may require maintaining the bone portions substantially immobilized relative to each other.

In one embodiment, a compact anti-rotation device for securing adjacent bones and preventing or impeding such bones from relative rotation thereof, to facilitate healing of the bones or tissue or ligaments connected thereto is described. The device includes a torsion bar having a first end and a second end. The torsion bar is sized and configured to twist and deform in response to a torque applied thereto. The device includes a first anchoring member coupled to or integrated with the first end of the torsion bar and a second anchoring member coupled to or integrated with the second end of the torsion bar. Each of the first anchoring member and the second anchoring member has a plurality of prongs oriented substantially perpendicularly to the torsion bar.

In some embodiments, each prong of the plurality of prongs is substantially parallel to other prongs of the plurality of prongs. A center axis of each prong of the plurality of prongs, in further embodiments, is approximately aligned with and perpendicular to a longitudinal axis of the torsion bar.

At least one prong of the plurality of prongs of the first anchoring member, in some embodiments, has a piercing tip located near or forming a distal end thereof. In further embodiments, each prong of the plurality of prongs has a piercing tip located near or forming a distal end thereof. In some embodiments, each prong of the plurality of prongs has a blade-like configuration. Each of the first and second anchoring members, in further embodiments, comprises two prongs.

In another embodiment, a system for securing adjacent bones and preventing such bones from relative rotation, to facilitate healing of the bones or tissue or ligaments connected thereto is described. The system includes one or more elongated inner connectors sized and configured to be embedded in the adjacent bones. The one or more elongated inner connectors are further sized and configured to guide and orient the adjacent bones relative to each other. The system includes a compact anti-rotation device. The compact anti-rotation device includes at least one torsion bar having a substantially linear shape, a first anchoring member coupled to or integrated with the at least one torsion bar, and a second anchoring member coupled to or integrated with the at least one torsion bar, wherein the first and second anchoring members comprise a plurality of prongs.

In some embodiments, each prong of the plurality of prongs is oriented substantially perpendicular to the at least one torsion bar. The plurality of prongs, in further embodiments, are positioned in line with one another.

A center axis of each prong of the plurality of prongs, in some embodiments, is approximately aligned with and perpendicular to a longitudinal axis of the at least one torsion bar. In further embodiments, the one or more elongated inner connectors comprise a first K-wire and a second K-wire.

In some embodiments, the one or more elongated inner connectors comprise a bone screw. The adjacent bone portions, in further embodiments, comprise a scaphoid bone and a lunate bone.

In another embodiment, a method of immobilizing and securing adjacent bones and preventing such bones from relative rotation, to facilitate healing of the bones or tissue or ligaments connected thereto is described. The method includes positioning a first bone and a second, adjacent bone at desired locations relative to each other. At least one elongated inner connector is inserted through the first bone and through the second bone, thereby fixing the desired location of the first and second bones relative to each other. A first anchor of a compact anti-rotation device is inserted through a first outer surface of the first bone and into the first bone. A second anchor of the compact anti-rotation device is inserted through a second outer surface of the second bone and into the second bone.

In some embodiments, the first bone comprises a scaphoid bone and the second bone comprises a lunate bone. Inserting the at least one elongated inner connector through the first bone and through the second bone, in further embodiments, includes inserting a first K-wire and a second K-wire through the scaphoid and lunate bones.

Inserting the first anchor of a compact anti-rotation device through a first outer surface of the first bone and into the first bone, in some embodiments, comprises inserting a first plurality of prongs that define the first anchor into the scaphoid bone. In further embodiments, the first plurality of prongs are inserted at an angle substantially perpendicular to an axis of rotation of a joint defined by the scaphoid and lunate bones. In yet further embodiments, inserting the second anchor of the compact anti-rotation device through a second outer surface of the second bone and into the second bone comprises inserting a second plurality of prongs that define the second anchor into the lunate bone.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1A:
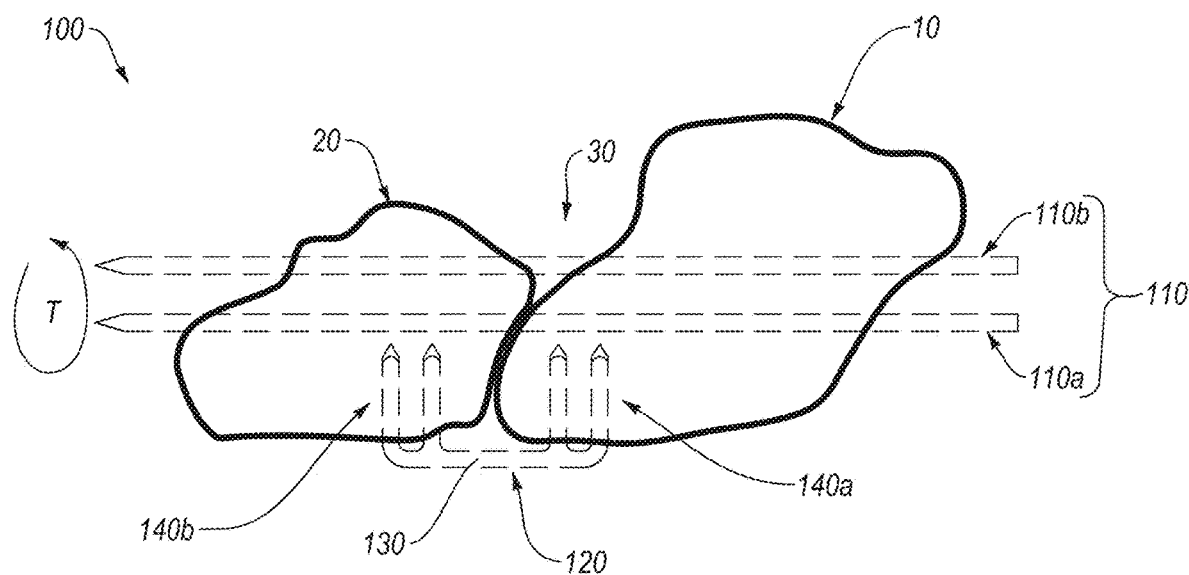
FIG. 1A illustrates a side view of an immobilization system deployed in scaphoid and lunate bones in accordance with one embodiment of the present invention.

Embodiments of the present invention provide systems, methods, and apparatus for immobilizing and/or securing bone portions. Particularly, at least one embodiment involves a compact anti-rotation device that can secure adjacent bones and/or bone portions in a manner that prevents or limits relative rotational and bending movement thereof. Accordingly, the compact anti-rotation device can help promote healing of reconnected bone portions, which may require maintaining the bone portions in a substantially immobilized state relative to each other. For example, the bone portions may be restricted from moving relative to each other, such that some slight movement is allowed, but any major movement is prevented.

In one example, the compact anti-rotation device can include a torsion bar and anchoring members on opposing sides thereof. Such anchoring members can be secured to the bone portions, thereby immobilizing the bone portion and preventing or limiting rotation of the bone portions relative to each other. For instance, the compact anti-rotation device can have a first anchoring member coupled to or integrated with a first end of the torsion bar and a second anchoring member coupled to or integrated with a second end of the torsion bar. As further described below, insufficient anchoring of the torsion bar can lead to bending or twisting of the anchoring members relative to the torsion bar instead of torquing or twisting the torsion bar.

In one embodiment, the anchoring members can be inserted or embedded into the bone portions. Moreover, the anchoring members can be configured in a manner that the anchoring members can resist rotation within the bone portions. For example, each anchoring member can comprise multiple prongs protruding from the torsion bar of the compact anti-rotation device. Multiple prongs can resist or prevent rotation of the anchoring members within the bone portions, as further described below. In some embodiments, the prongs can be inserted through an outer surface of the bone portions, such that the torsion bar remains outside of the bone portions.

Embodiments also include an immobilization system that can be employed for securing adjacent bone portions. Such a system or kit can incorporate one or more elongated inner connectors (e.g., K-wires, screws, etc.) that can be placed or embedded within the bone portions. The system also can include the compact anti-rotation device, portions of which can be embedded inside the bone portions, through an outer surface thereof. As such, the elongated inner connectors can connect and locate the bone portions in anatomically correct or desirable positions relative to each other and can at least partially restrict relative lateral and/or rotational movement of the bone portions. The compact anti-rotation device can further reinforce the connection between the bone portions and can provide sufficient immobilization therebetween to facilitate healing (e.g., healing of a repaired ligament between the bone portions).

In one embodiment, the immobilization system and/or device can be used to repair scapholunate joint. In particular, the immobilization system and/or device can be used to secure and or immobilize scaphoid and lunate bones (e.g., after repairing the scapholunate ligament). As mentioned above, such immobilization can sufficiently restrain the scaphoid and lunate bones from rotating relative to each other, which can facilitate healing of the repaired ligament.

Figure 1B:
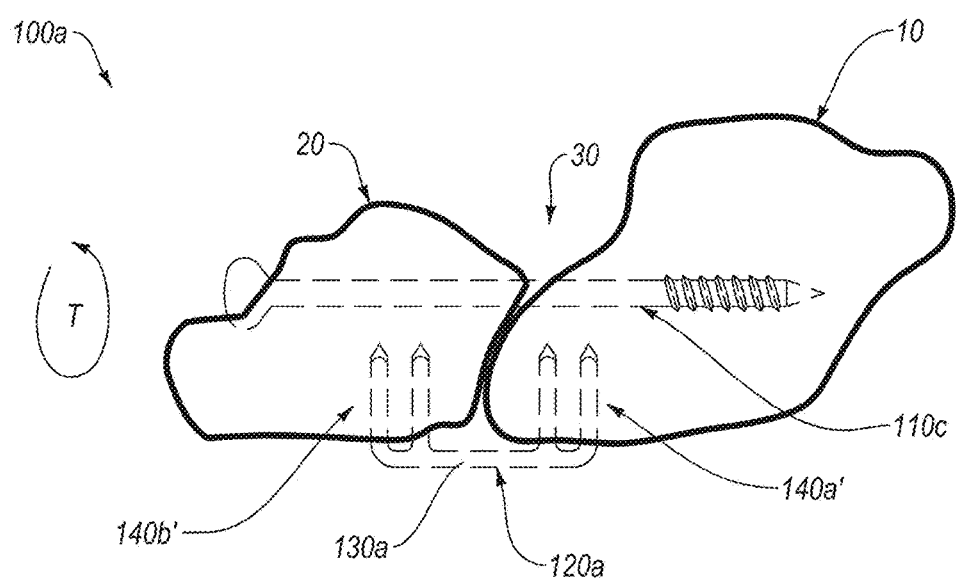
FIG. 1B illustrates a side view of an immobilization system deployed in scaphoid and lunate bones in accordance with another embodiment of the present invention.

FIGS. 1A-1B illustrate exemplary deployments of compact anti-rotation devices and systems. Specifically, FIG. 1A illustrates the scaphoid bone 10 and the lunate bone 20 secured together by an immobilization system 100. For instance, the immobilization system 100 can include one or more elongated internal connectors 110 (e.g., K-wires 110a, 110b). The immobilization system 100 also can include a compact anti-rotation device 120, which can further secure the scaphoid bone 10 and the lunate bone 20 together.

Particularly, the compact anti-rotation device 120 can aid in preventing the scaphoid bone 10 and the lunate bone 20 from rotating relative to each other. Relative rotation (and/or other relative movement) of the scaphoid bone 10 and the lunate bone 20 can disrupt a newly repaired ligament. Accordingly, providing sufficient immobilization of the scaphoid bone 10 and the lunate bone 20 can improve healing of the repaired ligament.

More specifically, as the patient rotates a wrist that has the recently repaired scaphoid bone 10 and the lunate bone 20, a torque T can be applied to the scapholunate joint 30, which typically tends to rotate the scaphoid bone 10 and the lunate bone 20 relative to each other. For instance, a 50° rotation of the wrist can result in approximately 10° differential rotation of the scaphoid bone 10 and the lunate bone 20. As noted above, the torque T can result in relative rotation of the scaphoid bone 10 and the lunate bone 20, which may disrupt the healing process of a recently repaired scapholunate ligament. Hence, in one or more embodiments, the immobilization system 100 can sufficiently counteract the torque T to prevent or limit such rotation. For instance, in one or more embodiments, the immobilization system 100 can limit such rotation of the scaphoid bone 10 relative to the lunate bone 20 to less than 10°, 5°, 2°, or 0.5°. In one example, the immobilization system 100 can prevent or limit relative rotation of scaphoid and lunate bones 10, 20 to less than about 1° in response to an applied torque of approximately 200 N-mm.

In some embodiments, the compact anti-rotation device 120 can comprise a torsion bar 130 and opposing anchoring members 140a, 140b that can couple the torsion bar 130 to the scaphoid bone 10 and the lunate bone 20, respectively, thereby securing the scaphoid bone 10 and the lunate bone 20 together. In at least one embodiment, the anchoring member 140a and/or the anchoring member 140b can be configured to prevent rotation thereof inside the respective scaphoid bone 10 and the lunate bone 20. It should be appreciated that, as described in more detail below in connection with experimental data, commonly used devices can be prone to rotation within the scaphoid bone 10 and the lunate bone 20 when torque perpendicular to the scapholunate joint 30 is applied thereto. Accordingly, at least one embodiment of the present invention provides for limiting or preventing rotation of the anchoring members 140a, 140b, which can improve efficacy of the compact anti-rotation device 120 in limiting or preventing rotation of the scaphoid bone 10 and the lunate bone 20 relative to each other.

In some embodiments, the anchoring members 140a, 140b can have multiple prongs that can be inserted into the scaphoid bone 10 and the lunate bone 20, respectively. The multiple prongs can limit or eliminate rotation of the anchoring members 140a, 140b within the bones, as respective axes of the prongs can be separated by a distance. As such, the prongs can resist rotating within the scaphoid and lunate bones 10, 20.

Therefore, as the anchoring members 140a, 140b can remain substantially fixed relative to the respective scaphoid bone 10 and the lunate bone 20, the anchoring members 140a, 140b can apply torque onto the torsion bar 130, as the scaphoid and lunate bones 10, 20 attempt to rotate relative to each other. As the torque is applied, the torsion bar 130 can twist, thereby deforming substantially along the entire length thereof. In some embodiments, such deformation can be elastic, such that the torsion bar 130 can return substantially to its un-deformed configuration after the torque is removed (e.g., after the scaphoid bone 10 and the lunate bone 20 are rotated back to their original relative positions). Alternatively, the torsion bar 130 can plastically deform in response to the applied torque, thereby maintaining the deformed configuration after the torque is removed.

It should be appreciated that whether the torsion bar 130 experiences an elastic or plastic deformation can vary from one embodiment to another. Moreover, in some instances the torsion bar 130 can elastically deform in response to a twist to a predetermined first angle. The same torsion bar 130 also can plastically deform in response to a twist to another angle, which is greater than the first angle.

In light of this disclosure it should be appreciated that joints, which can be secured by the compact anti-rotation device 120, can be under stress or strain in response to ordinary movements of the patient. For instance, the scapholunate joint 30 can be placed under strain in multiple planes during ordinary movement of the patient's wrist. In other words, as mentioned above, the scaphoid bone 10 and the lunate bone 20 can rotate relative to each other, which can place the scapholunate joint 30 under strain. Furthermore, the scaphoid and lunate bones 10, 20 typically have small surface areas, which contribute to difficulty of securing the scaphoid bone 10 relative to the lunate bone 20 in a manner that can prevent relative rotation thereof and facilitate healing.

Accordingly, at least one embodiment of the compact anti-rotation device 120 can be sufficiently small or compact as well as resilient to facilitate attachment thereof to the scaphoid and lunate bones 10, 20 and to prevent or impede relative rotation of thereof. Hence, in at least one embodiment, the anchoring members 140a, 140b can be sufficiently small or compact as to securely couple to the scaphoid bone 10 and the lunate bone 20, respectively. Likewise, the torsion bar 130 can be sufficiently compact such as to facilitate attachment of the compact anti-rotation device 120 to the scaphoid and lunate bones 10, 20.

In light of this disclosure, it should be appreciated that "compactness" referenced herein is a measure that is relative to the size of the scaphoid and lunate bones 10, 20 as well as to generally available space in the region of the patient's wrist. For example, the compact anti-rotation device 120 can have a length in the range of 10 mm to 13 mm, 11 mm to 18 mm, 15 mm to 20 mm, and 19 mm to 25 mm. Preferably, the length of the compact anti-rotation device 120 can be about 22 mm. In some embodiments, the length of the compact anti-rotation device 120 can be greater than 25 mm or less than 10 mm. The compact anti-rotation device 120 also can have a thickness in the range of 1 mm to 5 mm, 3 mm to 8 mm, and 7 mm to 10 mm. In one or more embodiments, however, the thickness of the compact anti-rotation device 120 can be greater than 10 mm or less than 1 mm.

In some embodiments, at least a portion of the anchoring members 140*a*, 140*b* can be inserted into the scaphoid bone 10 and the lunate bone 20, respectively. Accordingly, the compact anti-rotation device 120 can have a third dimension that can relate to the width thereof or to the maximum depth of penetration of the anchoring members 140*a*, 140*b* into the bone. Particular width of the compact anti-rotation device 120 can vary from one embodiment to another and can depend on location or position of the elongated internal connectors 110, such that the anchoring members 140*a*, 140*b* do not hit and/or damage the elongated internal connectors 110.

In one example, as described above, the elongated internal connectors 110 can comprise the K-wires 110*a*, 110*b*, which can have suitable diameters and lengths. For instance, the K-wires 110*a*, 110*b* can be standard-sized K-wires (e.g., 0.045" or 1.1 mm diameter). Moreover, spacing between the K-wires 110*a*, 110*b* also can vary from one embodiment to another. Embodiments of the present invention can include K-wires 110*a*, 110*b* having a spacing therebetween in the range of approximately 1 mm to 3 mm and 2 mm to 5 mm. In some embodiments, the spacing between the K-wires 110*a*, 110*b* can be greater than 5 mm or less than 1 mm. Specifically, among other considerations, the spacing between the K-wires 110*a*, 110*b* can depend upon the particular size and shape of the patient's scaphoid bone 10 and the lunate bone 20 as well as on the size of the K-wires 110*a*, 110*b*.

In any event, the K-wires 110*a*, 110*b* can locate and orient the scaphoid bone 10 and the lunate bone 20 relative to each other as well as at least partially immobilize the scaphoid and lunate bones 10, 20 from relative rotational movement. It should be appreciated that the greater the spacing between the K-wires 110*a*, 110*b*, the greater the resistance that can be provided to relative rotation of the scaphoid bone 10 and the lunate bone 20 (as discussed below in connection with experimental data). Increased spacing between the K-wires 110*a*, 110*b* also can limit the maximum possible depth of penetration by the anchoring members 140*a*, 140*b* into the respective scaphoid and lunate bones 10, 20, which can limit the maximum width of the compact anti-rotation device 120.

Some embodiments can include an elongated internal connector that can fasten the scaphoid bone 10 and the lunate bone 20 together in a secure manner. For example, FIG. 1B illustrates an immobilization system 100*a*, which includes an elongated internal connector that is a bone screw 110*c*. The immobilization system 100*a* and all of the components and elements thereof can be similar to or the same as the immobilization system 100 (FIG. 1A) and all of its respective components and elements, except as otherwise described herein. The bone screw 110*c* can securely couple together the scaphoid bone 10 and the lunate bone 20.

For instance, the bone screw 110*c* can be blind or an un-cannulated screw. Alternatively, the bone screw 110*c* can be a cannulated screw. Thus, in one or more embodiments, the cannulated bone screw 110*c* can slide over a K-wire, positioned inside the scaphoid bone 10 and/or inside the lunate bone 20. As such, the scaphoid and lunate bones 10, 20 can be placed into correct orientation, positions, and alignment relative to each other before the scaphoid bone 10 and the lunate bone 20 are secured together with the bone screw 110*c*.

In some instances, the bone screw 110*c* can provide greater resistance to decoupling or dissociation of the scaphoid and lunate bones 10, 20 from each other, as compared with the K-wires 110*a*, 110*b* (FIG. 1A). At the same time, however, as described below in experimental results, the bone screw 110*c* may provide less resistance to relative rotation of the scaphoid and lunate bones 10, 20 as compared with the K-wires 110*a*, 110*b* (FIG. 1A).

Additionally, in some embodiments, the bone screw 110*c* can allow for a compact anti-rotation device 120*a* with anchoring members 140*a'*, 140*b'* that can be longer than the anchoring members 140*a*, 140*b* of the compact anti-rotation device 120, as can be used in conjunction with the K-wires 110*a*, 110*b* of the immobilization system 100 (FIG. 1A). Accordingly, for instance, the compact anti-rotation device 120*a* also can incorporate a torsion bar 130*a* with a greater cross-sectional area than the torsion bar 130 of the compact anti-rotation device 120 (FIG. 1A). In other words, the larger anchoring members 140*a'*, 140*b'* can withstand greater torque without rotating within the scaphoid and lunate bones 10, 20. As such, the anchoring members 140*a'*, 140*b'* also can transfer more torque onto the torsion bar 130*a*; because the torsion bar 130*a* can be larger than the torsion bar 130 (FIG. 1A), the torsion bar 130*a* also can absorb and withstand a greater amount of torque T transferred thereto. Therefore, in at least one embodiment, the compact anti-rotation device 120*a* can be configured to provide sufficient anti-rotational reinforcement in the immobilization system 100*a* that incorporates the bone screw 110*c*.

Figure 2:
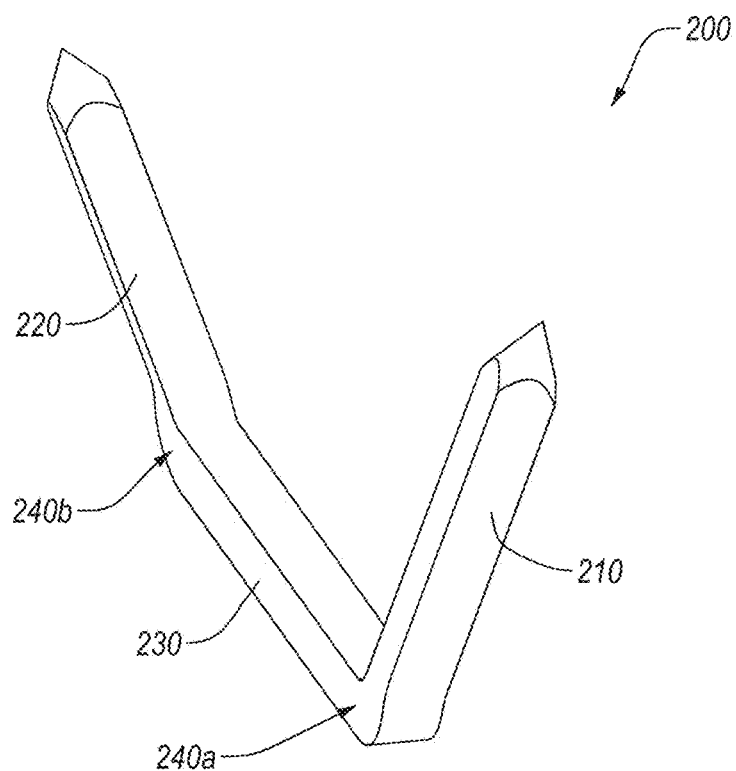
FIG. 2 illustrates a perspective view of a simple staple with bent or twisted opposing prongs.

In any event, as described above, the anchoring members 140*a'*, 140*b'* can be coupled to and/or inserted into the respective scaphoid and lunate bones 10, 20 in a manner that allows the anchoring members 140*a'*, 140*b'* to transfer torque T to the torsion bar 130*a*, thereby preventing or impeding relative rotation of the scaphoid and lunate bones 10, 20. By contrast, it should be appreciated that some anchoring members may be insufficiently secured within the scaphoid bone 10 and/or within the lunate bone 20. For example, FIG. 2 illustrates a standard staple 200 having opposing prongs 210, 220. The prongs 210, 220 can be coupled to or integrated with a connector or torsion bar 230.

As described below in the experimental results, the prongs 210, 220 of the staple 200 can rotate within the adjacent bones (e.g., within the scaphoid and lunate bones), for instance, when a torque is applied about a joint comprising such bones. In particular, rotation of the prongs 210, 220 within the scaphoid and lunate bones can prevent the prongs 210, 220 from transferring torque from the bones to the torsion bar 230. Consequently, instead of twisting the torsion bar 230, the toque transferred to the staple 200 can bend the prongs 210, 220 relative to the torsion bar 230 (e.g., at locations 240*a*, 240*b*). As such, the staple 200 can absorb less torque as compared with the compact anti-rotation device 120, 120*a* (FIGS. 1A, 1B) of the present invention.

Figure 3:
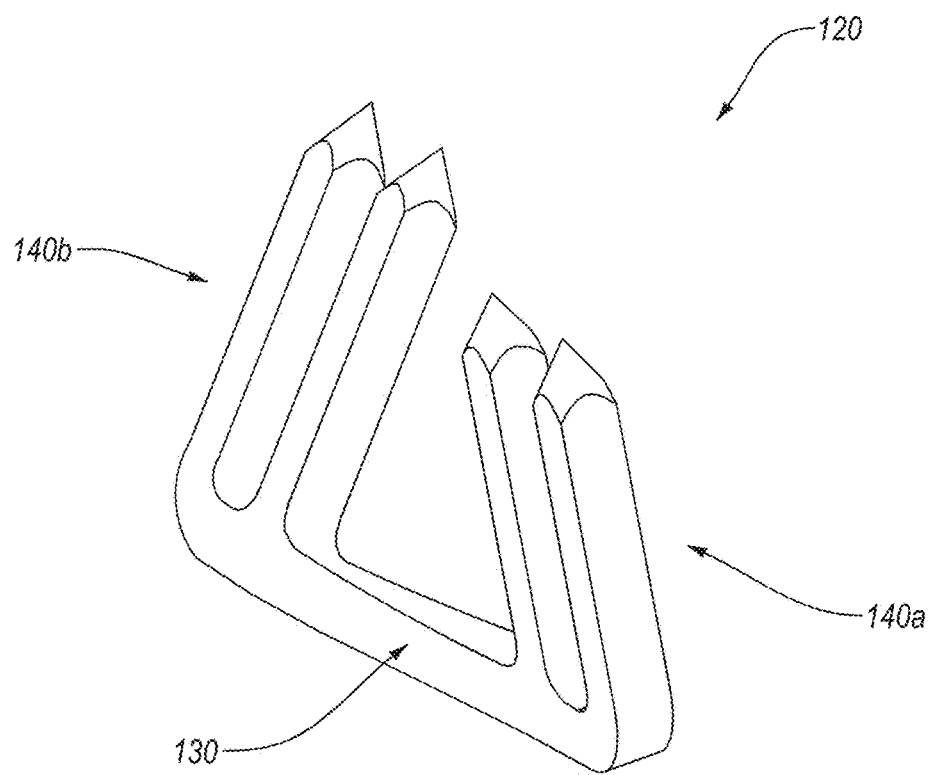
FIG. 3 illustrates a perspective view of a twisted compact anti-rotation device in accordance with one embodiment of the present invention.

In contrast to the staple 200, at least one embodiment of the present invention, as illustrated in FIG. 3, can incorporate the anchoring members 140*a*, 140*b* of the compact anti-rotation device 120, which can transfer torque applied to the scaphoid and lunate bones to the torsion bar 130. Accordingly, the torsion bar 130 can absorb more energy (as compared with the torsion bar 230 of the staple 200; FIG. 2), because the anchoring members 140*a*, 140*b* can remain substantially fixed within the scaphoid and lunate bones and, thus, can transfer the torque applied at the scapholunate joint to the torsion bar 130. Therefore, (as supported by experimental data provided below), the compact anti-rotation device 120 can provide a substantially greater anti-rotational resistance to the scaphoid and lunate bones (e.g., as compared with the standard staple 200).

Figure 4:
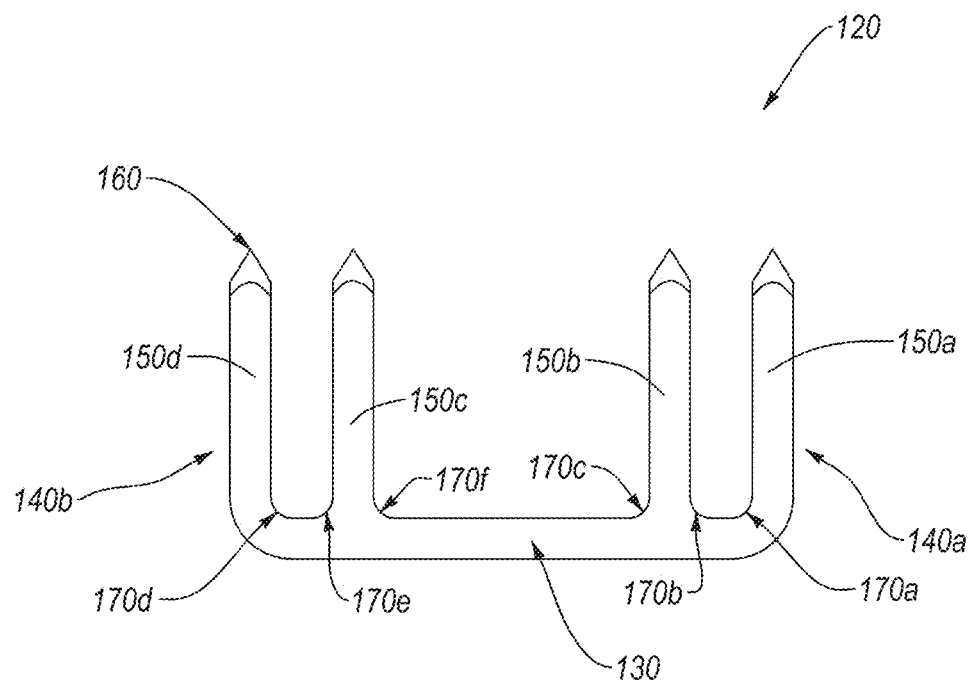
FIG. 4 illustrates a side view of an compact anti-rotation device in accordance with one embodiment of the present invention.

As noted above, the anchoring members 140a, 140b can be configured to be inserted into the scaphoid and lunate bones of the scapholunate joint. For instance, as illustrated in FIG. 4, the anchoring members 140a, 140b of the compact anti-rotation device 120 can comprise prongs 150a, 150b, 150c, 150d. More specifically, in some embodiments, the anchoring member 140a can comprise prongs 150a, 150b, and the anchoring member 140b can comprise prongs 150c, 150d. As mentioned above, the prongs 150a, 150b, 150c, 150d can be embedded into and secured within opposing bones, such as the scaphoid and lunate bones.

Thus, in at least one embodiment, distal ends of the prongs 150a, 150b, 150c, 150d can have piercing tips 160. In some instances, the compact anti-rotation device 120 can be implanted with an automated tool. Hence, the 160 can penetrate into the bone. Additionally or alternatively, holes corresponding with the prongs 150a, 150b, 150c, 150d can be predrilled in the bones and the prongs 150a, 150b, 150c, 150d of the compact anti-rotation device 120 can be inserted or tapped into those holes. Consequently, in some embodiments, the distal ends of the prongs 150a, 150b, 150c, 150d can have any number of other suitable configurations which may or may not be the piercing tips 160.

Furthermore, at least one embodiment can include the prongs 150a, 150b, 150c, 150d that incorporate bars, spikes, or other protrusions that can aid in securing the prongs 150a, 150b, 150c, 150d within the bone. For instance, tapered barbs can be disposed along the lengths of each of the prongs 150a, 150b, 150c, 150d. Alternatively, the prongs 150a, 150b, 150c, 150d can be substantially flat or straight and can have a substantially smooth surface.

Additionally, the prongs 150a, 150b, 150c, 150d have a substantially orthogonal orientation with respect to the torsion bar 130. Moreover, in one or more embodiments, the prongs 150a, 150b, 150c, 150d also can be substantially parallel relative to each other. Accordingly, parallel orientation of the prongs 150a, 150b, 150c, 150d can allow the compact anti-rotation device 120 to be inserted in a single, substantially linear movement. Furthermore, the prongs 150a, 150b, 150c, 150d can be positioned substantially in the same line as one another as well as concentrically with respect to a longitudinal axis extending through the torsion bar 130. Concentric positioning of the prongs 150a, 150b, 150c, 150d with the torsion bar 130 can optimize transmittal of torque from the prongs 150a, 150b, 150c, 150d onto the torsion bar 130.

Also, it should be noted that perpendicular orientation of the prongs 150a, 150b, 150c, 150d relative to the torsion bar 130 can facilitate placement of the compact anti-rotation device 120 in a manner that the torsion bar 130 remains outside of the scaphoid and lunate bones, while the prongs 150a, 150b, 150c, 150d are embedded inside of the bones. In other words, positioning the torsion bar 130 approximately parallel to the axis of rotation (as shown and described in connection with FIG. 7 below) at the scapholunate joint can be easier than for differently configured devices. Specifically, a user can orient the prongs 150a, 150b, 150c, 150d approximately perpendicular to the axis of rotation and can thereafter deploy the compact anti-rotation device 120.

In one embodiment, holes for accommodating the prongs 150a, 150b, 150c, 150d can be predrilled at approximately the same angles and approximately perpendicular to the axis of rotation. Without measuring tools and/or supplemental equipment, positioning the prongs 150a, 150b, 150c, 150d and/or drilling the holes in the bones at approximately orthogonal orientation can be easier than performing the same acts at other (i.e., acute or obtuse) angles. That is, non-orthogonal angles can be difficult and/or impractical or impossible to estimate with sufficient accuracy and can increase the degree of difficulty in deploying the anti-rotation device.

As described above, the width of the compact anti-rotation device 120 can vary from one embodiment to another and can depend, among other things, on the length of the prongs 150a, 150b, 150c, 150d. For example, the length of the prongs 150a, 150b, 150c, 150d can be in the range of 5 mm to 8 mm, 7 mm to 10 mm, and 9 mm to 15 mm. Preferably, the length of the prongs can be about 10 mm. It should be appreciated, however, that, in some embodiments, the length of the prongs 150a, 150b, 150c, 150d can be less than 5 mm or greater than 10 mm.

The prongs 150a, 150b, 150c, 150d of the compact anti-rotation device 120 also can have any number of suitable distances therebetween. In one embodiment, spaces between the prongs 150a, 150b and the spaces between the prongs 150c, 150d can be substantially the same. For instance, the prongs 150a, 150b can be spaced at approximately 1.8 mm. Other embodiments can include spaces between the prongs 150a and 150b that are greater or less than 1.8 mm.

In at least one embodiment, the compact anti-rotation device 120 also can have transition radii between the torsion bar 130 and the prongs 150a, 150b, 150c, 150d. Specifically, the compact anti-rotation device 120 can include transition radii 170a, 170b, 170c between the torsion bar 130 and the prongs 150a, 150b. Similarly, the compact anti-rotation device 120 can have transition radii 170d, 170e, 170f between the torsion bar 130 and the prongs 150c, 150d. The transition radii 170a, 170b, 170c, 170d, 170e, 170f can help reduce the stress at the transition or connection point between the torsion bar 130 and the prongs 150a, 150b, 150c, 150d. Accordingly, the transition radii 170a, 170b, 170c, 170d, 170e, 170f can increase the strength of the compact anti-rotation device 120 as well as the maximum amount of torque that the anchoring members 140a, 140b can transfer to the torsion bar 130.

Although the above embodiments describe the compact anti-rotation device 120 as having two prongs one each end thereof, it is to be appreciated that this invention is not so limited. Particularly, the anchoring members of the compact anti-rotation device can have more than two prongs, which can vary from one embodiment to the next. In at least one embodiment, the compact anti-rotation device can have three, four, or a greater number of prongs one any one end thereof. Moreover, as described below, the prongs can have any number of suitable shapes and configurations, such as to form the anchoring members of the compact anti-rotation device, which can remains substantially fixed within the bone.

The compact anti-rotation device 120 also can comprise any number of suitable materials, composites, or combinations thereof. In one embodiment, the compact anti-rotation device 120 can comprise a Nickel titanium alloy (also known as Nitinol®). Additionally or alternatively, the compact anti-rotation device 120 can comprise any suitable biodegradable, bioresorbable, or bioabsorbable material. For example, at least a portion of the compact anti-rotation device 120 may be made of poly-L-lactic acid, PLLA (polylactic acid), PGA (polyglycolic acid), a copolymer such as PLLA-PGA, other biodegradable, bioresorbable, or bioabsorbable materials, or combinations and/or composites thereof. Furthermore, the compact anti-rotation device 120 can comprise multiple materials, which can be coupled or fused together to from the compact anti-rotation device 120. In one example, the torsion bar 130 may be formed of one material and the anchoring members 140a, 140b may be formed of another material. For instance, the torsion bar 130 may be formed of a biodegradable, bioresorbable, or bioabsorbable material while the anchoring members may be formed of a Nickel titanium alloy. Also, the compact anti-rotation device 120 can be coated with a beneficial agent (e.g., anti-inflammatory, antibacterial, etc.), such as agents that can promote bone adhesion to the implant, including hydroxyapitite, as well as agents to strengthen bone such as bone morphogenic proteins, or statins, other beneficial agents, or combinations thereof.

Figure 5:
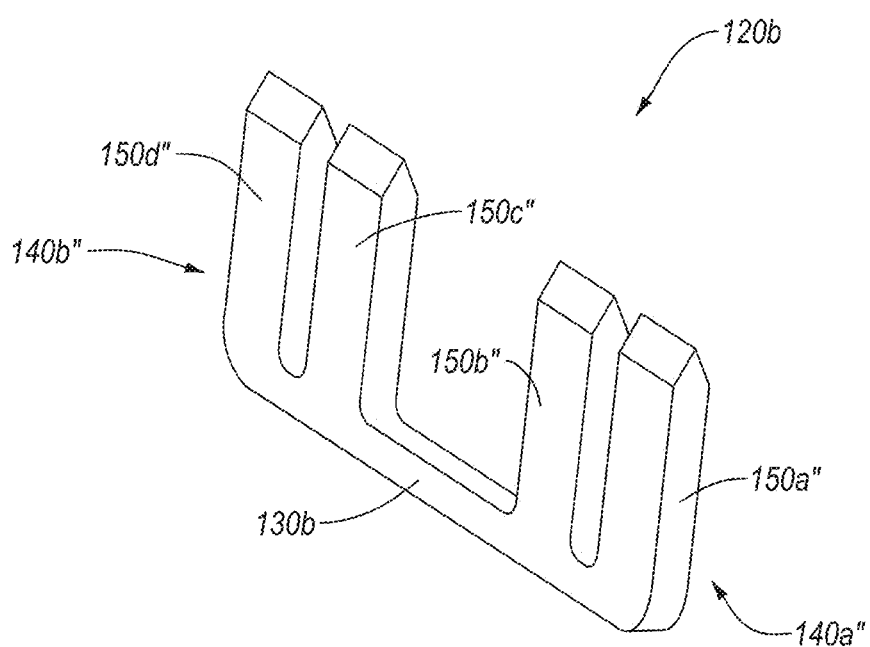
FIG. 5 illustrates a perspective view of an compact anti-rotation device in accordance with another embodiment of the present invention.

Resistance to deformation of the compact anti-rotation device can be increased by increasing the strength of the torsion bar 130 (e.g., by increasing the size or material thereof) and/or by increasing resistance of the anchoring members to rotation within the bone. For instance, as illustrated in FIG. 5, a compact anti-rotation device 120b can include anchoring members 140a", 140b" coupled to or integrated with a torsion bar 130b. Except as otherwise described herein, the compact anti-rotation device 120b and all of its components and elements can be similar to or the same as the compact anti-rotation devices 120, 120a (FIGS. 1A, 1B, 3) and all of their respective components and elements.

In one example, the compact anti-rotation device 120b can have blade-like prongs 150a", 150b", 150c", 150d". In particular, the blade-like prongs 150a", 150b", 150c", 150d" can have widths greater than thicknesses thereof. As such, the blade-like prongs 150a", 150b", 150c", 150d" can provide additional resistance to rotation within the bone and can transfer greater amount of torque to the torsion bar 130b.

Consequently, the compact anti-rotation device 120b also can incorporate the torsion bar 130b that has a higher strength than, for example, the torsion bar 130 (FIG. 1A). In some instance, deployment of the compact anti-rotation device 120b can be limited by the geometry of the bones as well as available in the area surrounding the bones. Accordingly, the compact anti-rotation device 120b can be deployed in bones and locations that provide sufficient space therefor.

Furthermore, embodiments of the present invention can include prongs of any number of configurations and shapes. For instance, the prongs can have a substantially cylindrical shape. Additionally or alternatively, in some embodiments, the prongs also can have a tubular shape.

Figure 6:
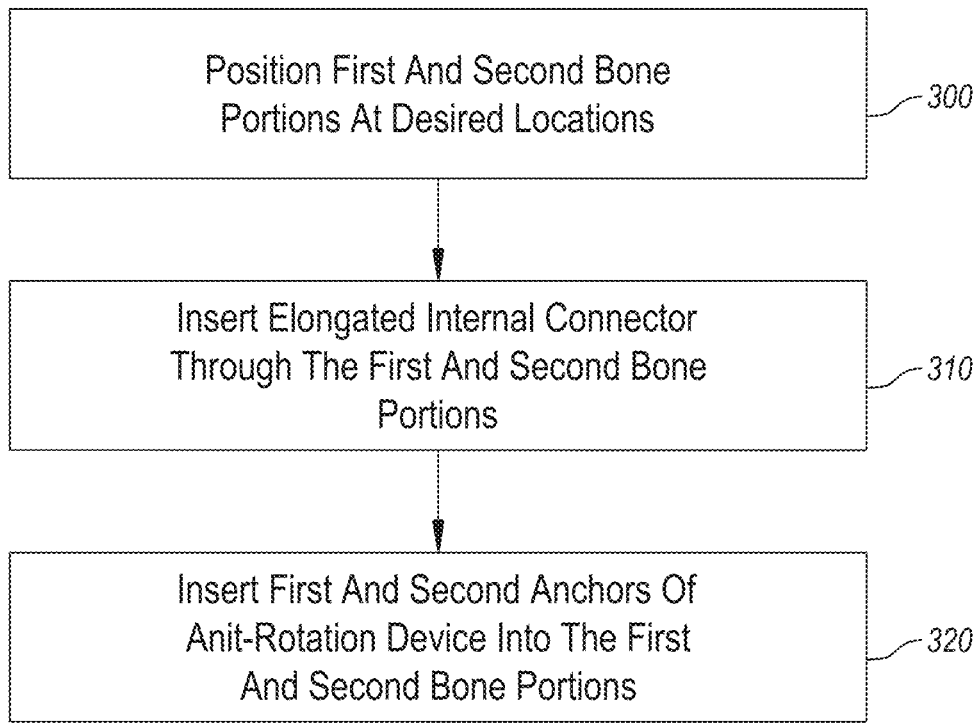
FIG. 6 illustrates a chart of acts for a method of immobilizing adjacent bones or bone portions in accordance with one embodiment of the present invention.

FIGS. 1A-1B and 3-5, and the corresponding text, provide a number of different components and mechanisms for securing and immobilizing adjacent bones (e.g., the scaphoid and lunate bones). In addition to the foregoing, embodiments of the present invention also can be described in terms of one or more acts in a method for accomplishing a particular result. For example, FIG. 6 illustrates a flowchart of one exemplary method for securing and immobilizing adjacent bones or bone portions relative to each other. The acts of FIG. 6 are described below with reference to the components of FIGS. 1A-1B and 3-5.

For example, FIG. 6 shows that one embodiment of the method of securing and immobilizing adjacent bones or bone portions can include an act 300 of positioning first and second bone portions at desired locations. In one embodiment, the first and second bone portions can comprise the scaphoid bone 10 and the lunate bone 20, respectively. For instance, the scaphoid bone 10 and the lunate bone 20 can be positioned at their respective normal (or pre-injury) anatomical locations.

The method also can include an act 310 of inserting the elongated internal connector 110 through the first and second bone portions. As noted above, at least some embodiments of the present invention also can include inserting multiple elongated internal connectors 110. Hence, for example, the act 310 can involve inserting the K-wires 110a, 110b. Additionally or alternatively, the act 310 can involve inserting the bone screw 110c. The elongated internal connector(s) 110 can align and orient the bone portions, such as the scaphoid bone 10 and the lunate bone 20, relative to each other. Furthermore, the elongated internal connector(s) 110 also can at least partially restrain and/or immobilize the bone portions from relative movement and/or rotation.

In addition, the method can include an act 320 of inserting first and second anchoring members (e.g., anchoring members 140a, 140b, 140a', 140b', 140a", 140b") of the compact anti-rotation device 120, 120a, 120b into the respective first and second bone portions, such as into the scaphoid bone 10 and the lunate bone 20. The anchoring members of the compact anti-rotation device 120, 120a, 120b can prevent or impede relative rotation of the scaphoid and lunate bones 10, 20. Accordingly, inserting or installing the elongated internal connector(s) 110 (e.g., K-wires 110a, 110b and/or bone screw 110c) as well as the compact anti-rotation device 120, 120a, 120b can help to immobilize the scaphoid bone 10 and the lunate bone 20, thereby facilitating healing thereof.

Experimental Data

Multiple specimens of scaphoid and lunate bone were tested. Specifically, the scaphoid and lunate bones were individually potted in aluminum cylinders using polymethylmethacrylate (PMMA). In preparation for potting, two perpendicular K-wires were placed in the most distal aspect of each scaphoid and lunate bones in a plane parallel to the scapholunate joint. These K-wires were only used to help anchor the specimen in the fixation pots and were not part of the scapholunate fixation hardware. Care was taken to ensure that these K-wires did not add to or interfere with the stability of the scapholunate fixation. Prior to potting, any exposed implant metal from the scapholunate fixation was covered with clay to prevent incorporation into the PMMA. The scaphoid bone was placed in a custom fabricated aluminum pot and held in place by four perpendicularly oriented screws. PMMA was then added to the pot and allowed to cure. The process was then repeated to secure the lunate bone in a separate custom aluminum pot.

Figure 7:
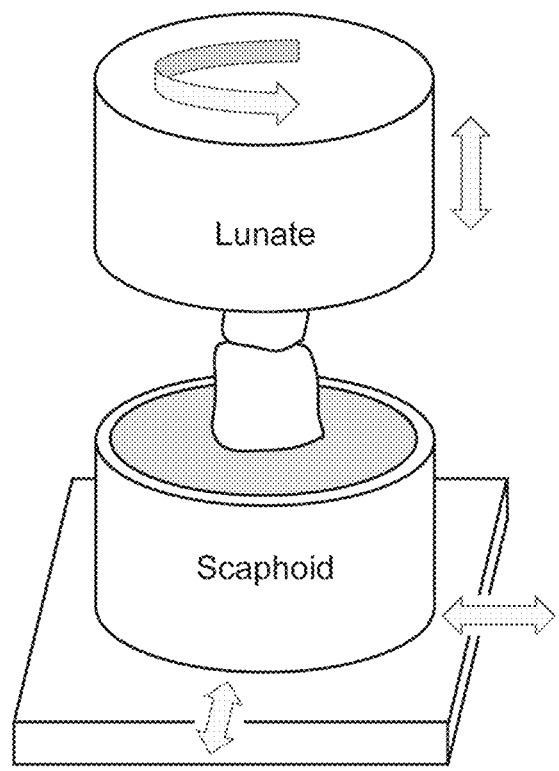
FIG. 7 illustrates a perspective view of a test setup used in experiments performed in connection with the present invention.

A bi-axial materials testing machine (MTS, Eden Prairie, MN) was used to test each scapholunate construct. As illustrated in FIG. 7, the potted scaphoid and lunate bones were secured in the testing machine and oriented in such a way as to allow the application of torque to the construct about an axis perpendicular to the scapholunate joint and approximately parallel to the centrally directed screw or K-wire fixation devices. Angular displacement was chosen as the control variable for testing with the resulting torque used as the primary outcome measure. Data was continuously collected at a rate of 100 samples per second. Axial compression across the joint was held constant at approximately zero, allowing the scapholunate joint to distract or compress freely in response to the torsional load. The potted lunate bone was rotated relative to the independently potted scaphoid bone. Torque was applied in a clockwise direction on the left hand specimens and in a counter-clockwise direction on the right hand specimens, about an axis perpendicular to the scapholunate joint, so as to cause the scaphoid bone to flex relative to the lunate bone. An X-Y table mounted in line with the axis of rotation allowed for substantially unconstrained motion of the scaphoid bone relative to the lunate bone in any direction perpendicular to the axis of rotation. Each specimen was rotated to 50 degrees, which is the failure point of the native scapholunate interosseous ligament ("SLIL") according to published literature. Statistical analysis of the data was done using ANOVA (Statistica) followed by Fisher LSD for comparisons. Significance was set at p=0.05.

Figure 8:
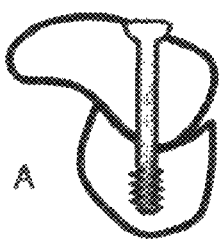
FIG. 8 illustrates side views of scaphoid and lunate bone pairs and immobilization devices and/or systems used in experiments performed in connection with the present invention.
Figure 8:
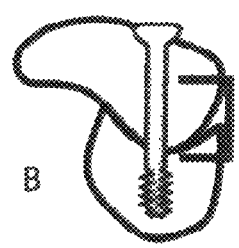
Figure 8:
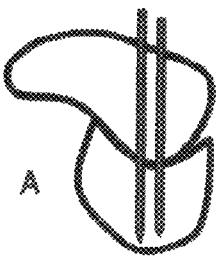
Figure 8:
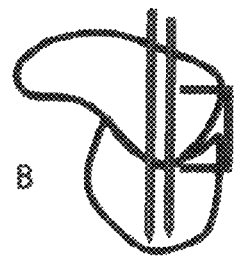
Figure 8:
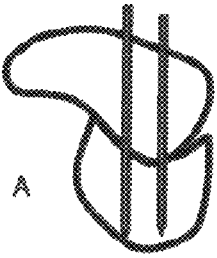
Figure 8:
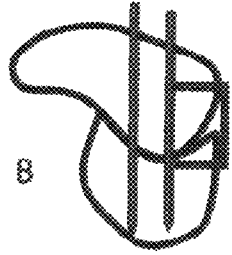
Figure 8:
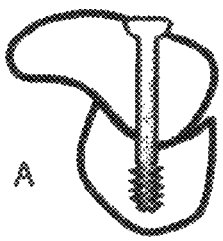
Figure 8:
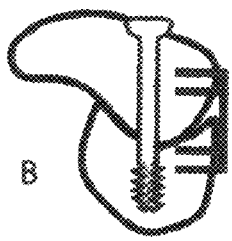
Figure 8:
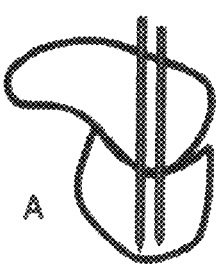
Figure 8:
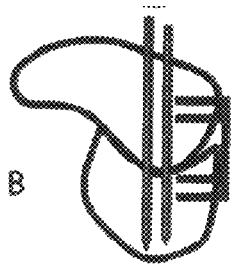
Figure 8:
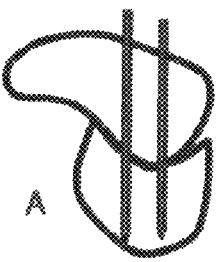
Figure 8:
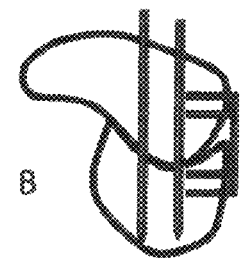

The compact anti-rotation device as well as a standard staple were used in the experiments. The standard staple refers to a standard 13×10 mm staple. The compact anti-rotation device was prepared by welding two standard (13×10 mm) staples to form a 22×10 mm compact anti-rotation device, having 1.8 mm separation between the outer prongs. The compact anti-rotation device produced the greatest resistance to relative rotation of the scaphoid and lunate bones in all of the traditional central fixation constructs analyzed in our study. Data, which was continually collected at a rate of 100 samples per second, is displayed at 5 and 10 degrees of angular displacement between the scaphoid and lunate bones in Table 1 below. The particular arrangements of the experimental groups identified in Table 1 are illustrated in FIG. 8.

substantial improvement in the amount of torque required to produce angular displacement at the scapholunate articulation. In addition, the compact anti-rotation device, although not statistically significant, provided approximately greater than 50% increased resistance to torsion at 5° and 10° when added to the 5.0 mm apart K-wire construct.

The compact anti-rotation device also outperformed the standard staple in each construct. The difference was most apparent and statistically significant when compared with the 3.0 mm screw and the 2.0 mm apart K-wire configuration. Augmentation with the compact anti-rotation device versus the standard staple at 5° in the 3.0 mm screw group produced approximately 3.1 times resistance to torque and approximately 1.1 times greater resistance with the compact anti-rotation device over the standard staple in the 2.0 mm apart K-wire group (p-value 0.0003 and 0.0285, respectively). Again, while not statistically significant, the addition

TABLE 1

| Experimental Group | Fixation Construct | At 5°: N-mm (st dev) | P Value | At 10°: N-mm (st dev) | P value |
|---|---|---|---|---|---|
| 1 | 3.0 mm screw | 81 (80) | 0.417 | 96 (107) | 0.177 |
|   | 3.0 mm screw + standard staple | 144 (82) |  | 244 (167) |  |
| 2 | 2.0 mm apart K-wires | 295 (213) | 0.0872 | 413 (252) | 0.0932 |
|   | 2.0 mm apart K-wires + standard staple | 388 (200) |  | 525 (240) |  |
| 3 | 5.0 mm apart K-wires | 384 (145) | 0.83 | 557 (223) | 0.69 |
|   | 5.0 mm apart K-wires + standard staple | 401 (140) |  | 600 (171) |  |
| 4 | 3.0 mm screw | 48 (22) | 0.0001 | 77 (45) | 0.0002 |
|   | 3.0 mm screw + custom staple | 453 (138) |  | 656 (182) |  |
| 5 | 2.0 mm apart K-wires | 247 (105) | 0.0035 | 402 (189) | 0.0030 |
|   | 2.0 mm apart K-wires + custom staple | 633 (167) |  | 879 (197) |  |
| 6 | 5.0 mm apart K-wires | 358 (161) | 0.1644 | 489 (212) | 0.1172 |
|   | 5.0 mm apart K-wires + custom staple | 601 (449) |  | 897 (650) |  |

When analyzed at 5°, the addition of the compact anti-rotation device with the 3.0 mm screw displayed approximately 9.4 times the resistance to torque as compared with the screw alone (p-value 0.0001). The addition of the compact anti-rotation device to the 2 mm apart K-wire configuration increased resistance to torsion by approximately 2.5 times when compared with the K-wire configuration alone (p-value 0.0035). Both of these represent a of the compact anti-rotation device versus the standard staple provided approximately greater than 60% increased resistance to torque in the 5 mm apart K-wire configuration.

When analyzing resistance to torque at the scapholunate articulation with the current traditional central fixation constructs, the lack of torsional stability afforded by the 3.0 mm screw becomes readily apparent, as can be seen in Table 2 below.

TABLE 2

(Comparison of the central fixation constructs alone).

| Experimental Group | Fixation Construct | At 5°: N-mm (st dev) | P-value | At 10°: N-mm (st dev) | P-value* |
|---|---|---|---|---|---|
| 4a | 3.0 mm screw | 48 (22) | 0.0005 | 77 (45) | 0.001 |
| 5a | 2.0 mm apart K-wires | 247 (105) |  | 402 (189) |  |
| 4a | 3.0 mm screw | 48 (22) | 0.0004 | 77 (45) | 0.0004 |
| 6a | 5.0 mm apart K-wires | 358 (161) |  | 489 (212) |  |
| 5a | 2.0 mm apart K-wires | 247 (105) | 0.1876 | 402 (189) | 0.4703 |
| 6a | 5.0 mm apart K-wires | 358 (161) |  | 489 (212) |  |

When the data is analyzed at 5°, the 3.0 mm screw provided approximately 48 N-mm resistance to torsion compared to 247 N-mm for the 2.0 mm apart K-wire and 358 N-mm for the 5.0 mm apart K-wire (p-values 0.005 and 0.0004, respectively). Although improved, we were not able to reach statistical significance when analyzing the difference in resistance to torsion between the 2.0 mm apart and 5.0 mm apart K-wire constructs. Of note these were not matched pairs and, therefore, may require increased power to reach statistical significance.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A method of immobilizing and securing a first bone and a second, adjacent bone and preventing said first bone and said second bone from relative rotation, to facilitate healing of said first bone and said second bone or tissue or ligaments connected thereto, the method comprising:
   positioning said first bone and said second, adjacent bone at desired locations relative to each other;
   inserting a first anchor of a compact anti-rotation device through a first outer surface of said first bone and into said first bone to create a first plurality of holes, the first anchor having a first plurality of prongs; and
   inserting a second anchor of the compact anti-rotation device through a second outer surface of said second bone and into said second bone to create a second plurality of holes, the compact anti-rotation device having a torsion bar extending between the first anchor and the second anchor to secure said first bone and said second, adjacent bone and to prevent said first bone and said second bone from relative rotation.

2. The method of claim 1, wherein the first plurality of prongs and a second plurality of prongs are positioned in one or more patterns concentric to a point on a longitudinal axis of the torsion bar.

3. The method of claim 1, wherein the torsion bar has a linear shape.

4. The method of claim 1, wherein one or more of the first plurality of prongs and a second plurality of prongs have a length of a range of 5 mm to 15 mm.

5. The method of claim 1, wherein one or more of the first plurality of prongs and a second plurality of prongs have a length of greater than 15 mm.

6. The method of claim 1, wherein one or more of the first plurality of prongs and a second plurality of prongs have a spacing from each other of less than 1.8 mm.

7. The method of claim 1, wherein the torsion bar has a polygonal cross section.

8. The method of claim 1, wherein the torsion bar is elongate.

9. The method of claim 1, wherein one or more of the first plurality of prongs or a second plurality of prongs are straight.

10. The method of claim 1, wherein one or more of the first plurality of prongs or a second plurality of prongs have smooth surfaces.

11. The method of claim 1, wherein the compact anti-rotation device is a Nickel titanium alloy.

12. The method of claim 1, wherein the first plurality of prongs and a second plurality of prongs have a spacing from each other of greater than 1.8 mm.

13. A method of securing a first bone and a second, adjacent bone and to facilitate healing of said first bone and said second bone or tissue or ligaments connected thereto, the method comprising:
   positioning said first bone and said second, adjacent bone at desired locations relative to each other;
   inserting at least one elongated inner connector through said first bone and through said second bone, thereby fixing the desired location of said first bone and said second bone relative to each other;
   inserting a first anchor of a compact anti-rotation device through a first outer surface of said first bone and into said first bone, wherein the first anchor includes a first plurality of prongs; and
   inserting a second anchor of the compact anti-rotation device through a second outer surface of said second bone and into said second bone to secure said first bone and said second, adjacent bone to facilitate healing of said first bone and said second bone or tissue or ligaments connected thereto.

14. The method as recited in claim 13, wherein said first bone comprises a scaphoid bone and said second bone comprises a lunate bone.

15. The method as recited in claim 14, wherein inserting the at least one elongated inner connector through said first bone and through said second bone comprises inserting a first K-wire and a second K-wire through said scaphoid bone and said lunate bone.

16. The method as recited in claim 15, wherein inserting the first anchor of the compact anti-rotation device through the first outer surface of said first bone and into said first bone comprises inserting the first plurality of prongs that define the first anchor into said scaphoid bone.

17. The method as recited in claim 16, wherein the first plurality of prongs are inserted at an angle perpendicular to an axis of rotation of a joint defined by said scaphoid bone and said lunate bone.

18. The method as recited in claim 16, wherein inserting the second anchor of the compact anti-rotation device through a second outer surface of said second bone and into said second bone comprises inserting a second plurality of prongs that define the second anchor into said lunate bone.

19. The method as recited in claim 13, wherein the second anchor includes a second plurality of prongs.

20. The method as recited in claim 13, wherein a torsion bar between the first anchor and the second anchor is straight before and after inserting the first anchor and inserting the second anchor.

21. The method of claim 13, wherein the first plurality of prongs and a second plurality of prongs are positioned in one or more patterns concentric to a point on a longitudinal axis of a torsion bar.

22. A method of securing adjacent bones and limiting such bones from relative rotation, to facilitate healing of the bones or tissue or ligaments connected thereto, the method comprising:
   positioning a first bone and a second, adjacent bone at desired locations relative to each other;
   inserting a first anchor of a compact anti-rotation device through a first outer surface of the first bone and into the first bone, wherein the first anchor includes a first plurality of prongs; and
   inserting a second anchor of the compact anti-rotation device through a second outer surface of the second bone and into the second bone to secure the first bone and the second, adjacent bone.

\* \* \* \* \*